(12) United States Patent
Goodman et al.

(10) Patent No.: US 10,420,901 B2
(45) Date of Patent: Sep. 24, 2019

(54) MINIMALLY CLOGGING DEVICE FOR DELIVERY OF FLUIDS

(71) Applicant: Ethicon, Inc., Somerville, NJ (US)

(72) Inventors: John Goodman, Ann Arbor, MI (US); Rebecca Leibowitz, Scotch Plains, NJ (US)

(73) Assignee: Ethicon, Inc., Somerville, NJ (US)

( * ) Notice: Subject to any disclaimer, the term of this patent is extended or adjusted under 35 U.S.C. 154(b) by 230 days.

(21) Appl. No.: 14/546,234

(22) Filed: Nov. 18, 2014

(65) Prior Publication Data

US 2016/0067423 A1 Mar. 10, 2016

Related U.S. Application Data

(60) Provisional application No. 62/045,883, filed on Sep. 4, 2014.

(51) Int. Cl.
| | |
|---|---|
| *A61M 5/32* | (2006.01) |
| *A61B 17/00* | (2006.01) |
| *B01F 5/06* | (2006.01) |
| *B01F 13/00* | (2006.01) |
| *B01F 15/00* | (2006.01) |
| *B05B 7/04* | (2006.01) |
| *B05B 15/522* | (2018.01) |

(52) U.S. Cl.
CPC ..... *A61M 5/3294* (2013.01); *A61B 17/00491* (2013.01); *A61M 5/3202* (2013.01); *B01F 5/0657* (2013.01); *B01F 13/0027* (2013.01); *B01F 15/00051* (2013.01); *B05B 7/0408* (2013.01); *B05B 15/522* (2018.02); *A61B 2017/00495* (2013.01)

(58) Field of Classification Search
CPC . A61M 5/3294; A61M 5/3202; B05B 15/522; B05B 7/0408; B05B 1/3006; A61B 17/00491; B01F 5/0657; B01F 13/0027; B01F 15/00051
USPC ............ 239/434.5, 403, 405, 406, 433, 491; 222/134, 135, 145.5, 145.7, 153.1, 541.5
See application file for complete search history.

(56) References Cited

U.S. PATENT DOCUMENTS 2,112,160 A * 3/1938 Johnson .................. A61M 5/19
24/546
3,395,344 A 7/1968 Bader
(Continued)

FOREIGN PATENT DOCUMENTS

| CN | 2560364 | 7/2003 |
|---|---|---|
| CN | 102039233 | 5/2011 |

(Continued)

OTHER PUBLICATIONS

International Preliminary Report on Patentability re: PCT/US2013/059119 dated Mar. 17, 2015.
(Continued)

*Primary Examiner* — Steven J Ganey
(74) *Attorney, Agent, or Firm* — David R. Crichton; Leo B. Kriksunov

(57) ABSTRACT

An apparatus and method for delivery of fluids, particularly biological, reactive fluids. The apparatus provides an opening when force is acted on the apparatus, and closure when no force is acted thereon. The apparatus provides a cleaning mechanism to remove fluids and other materials from a mixing space after use.

10 Claims, 8 Drawing Sheets

(56) References Cited

U.S. PATENT DOCUMENTS

| | | |
|---|---|---|
| 3,581,940 A | 6/1971 | Cella |
| 3,818,907 A | 6/1974 | Walton |
| 5,116,315 A * | 5/1992 | Capozzi ............ A61B 17/00491 |
| | | 222/137 |
| 5,605,255 A | 2/1997 | Reidel et al. |
| 6,063,055 A * | 5/2000 | Epstein ............ A61B 17/00491 |
| | | 604/191 |
| 6,328,229 B1 | 12/2001 | Duronio et al. |
| 6,341,735 B1 | 1/2002 | Baudin |
| 6,840,462 B2 | 1/2005 | Hurray et al. |
| 6,884,232 B1 | 4/2005 | Hagmann et al. |
| 6,974,053 B2 * | 12/2005 | Lautre ................ B65D 47/2081 |
| | | 222/212 |
| 8,033,483 B2 | 10/2011 | Fortier et al. |
| 8,210,453 B2 * | 7/2012 | Hull ................ A61B 17/00491 |
| | | 239/400 |
| 8,408,480 B2 | 4/2013 | Hull et al. |
| 8,657,780 B2 | 2/2014 | Palmer-Felgate |
| 2004/0092864 A1 | 5/2004 | Boehm, Jr. et al. |
| 2010/0096481 A1 * | 4/2010 | Hull ................ A61B 17/00491 |
| | | 239/600 |
| 2010/0330589 A1 * | 12/2010 | Bahrami ............ A61M 5/1452 |
| | | 435/7.9 |
| 2011/0319930 A1 | 12/2011 | Roush et al. |
| 2014/0074154 A1 | 3/2014 | Goodman et al. |
| 2015/0112248 A1 * | 4/2015 | Helliwell ............... A61B 5/065 |
| | | 604/28 |

FOREIGN PATENT DOCUMENTS

| | | |
|---|---|---|
| CN | 201959347 | 9/2011 |
| CN | 101801444 | 6/2013 |
| EA | 589 | 12/1999 |
| EP | 2163204 | 3/2010 |
| JP | 8-10329 | 1/1996 |
| JP | 3063935 | 9/1999 |
| JP | 2011-83615 | 4/2011 |
| RU | 2244559 | 1/2005 |
| RU | 2429056 | 9/2011 |
| RU | 142486 | 6/2014 |
| WO | WO 2000/018469 | 4/2000 |
| WO | WO 2003/080461 | 10/2003 |
| WO | WO 2005/091720 | 10/2005 |

OTHER PUBLICATIONS

International Search Report re: PCT/US2014/066150 dated May 8, 2015.
Written Opinion re: PCT/US2014/066150 dated May 8, 2015.

* cited by examiner

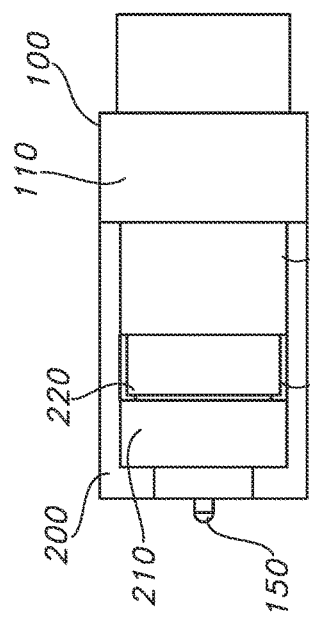
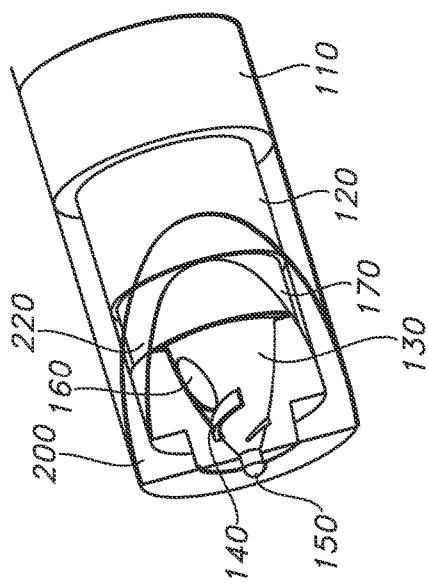
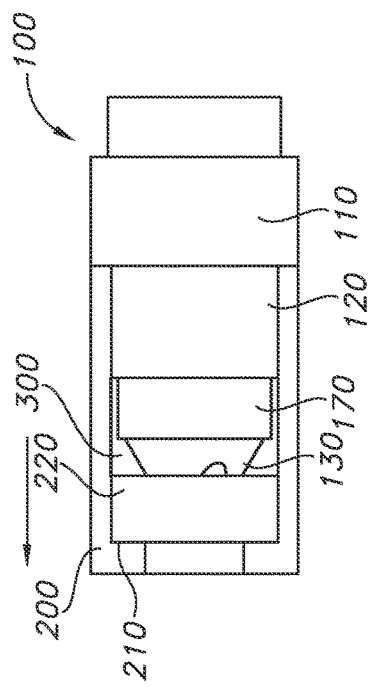
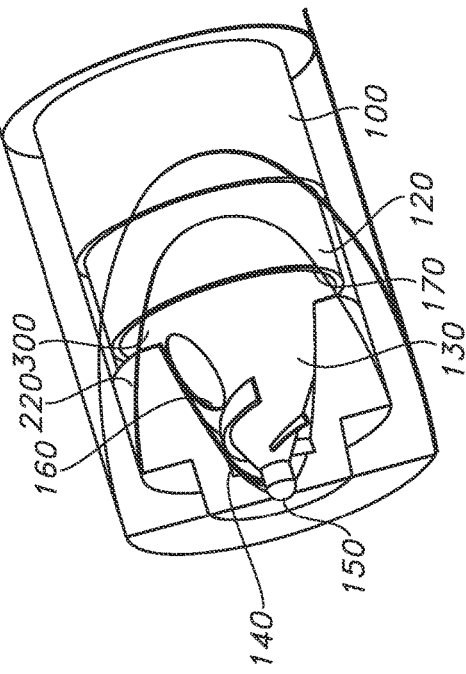

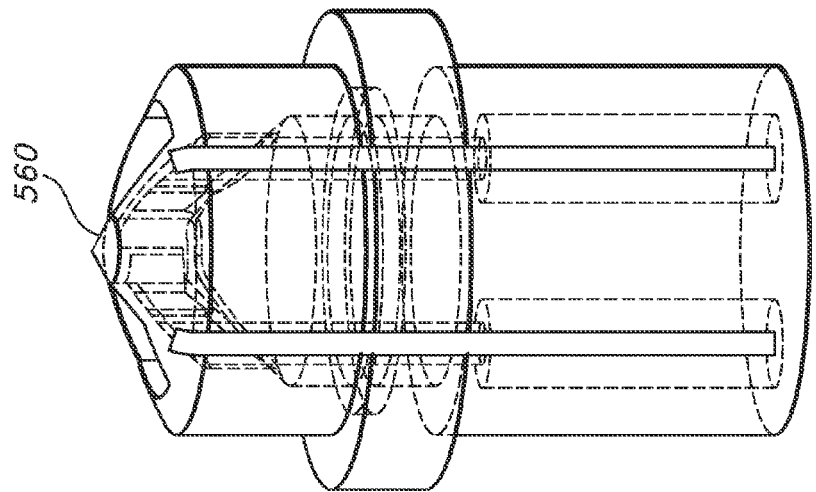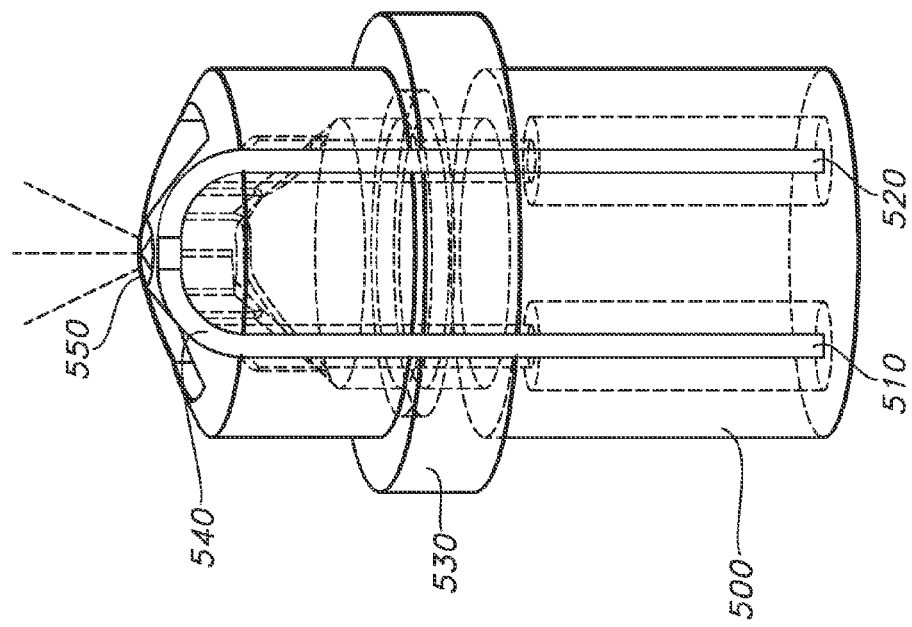

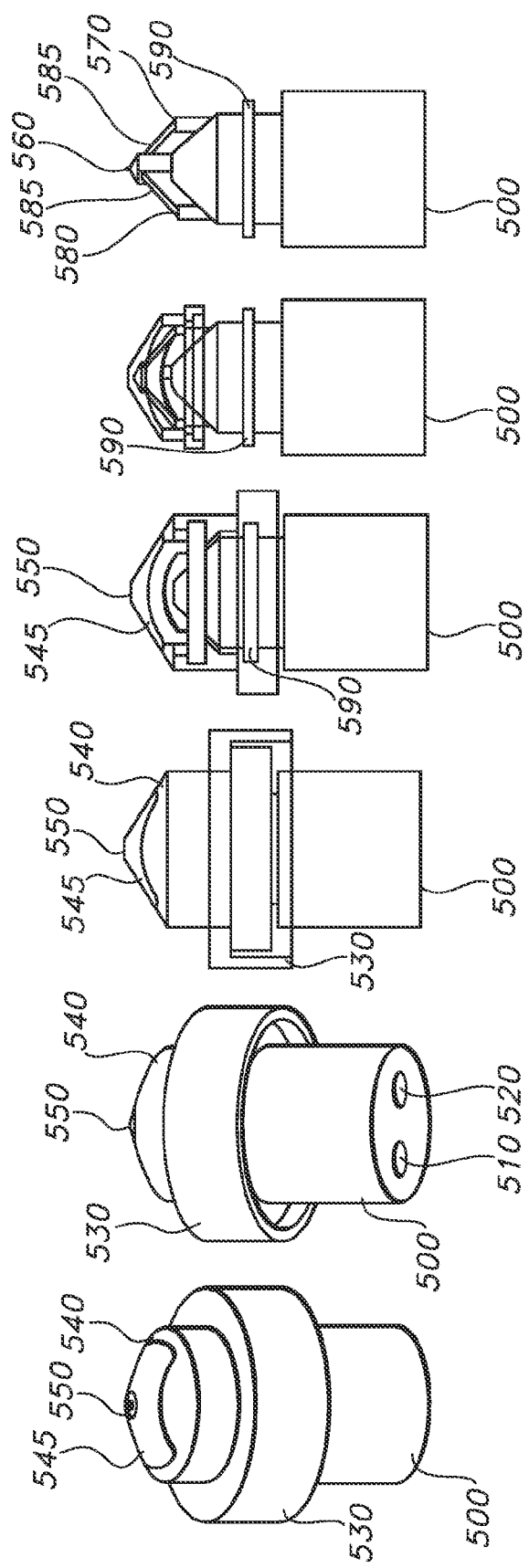

MINIMALLY CLOGGING DEVICE FOR DELIVERY OF FLUIDS

FIELD OF THE INVENTION

The present invention relates to tips and covers for dispensing of fluid materials, including a plurality of fluid materials that are mixed together to form a resulting product to be dispensed. The inventive tips and covers allow for secure dispensing of materials and subsequent sealing of the delivery port or ports when dispensing is complete.

BACKGROUND

Devices for dispensing two or more biocomponents are known. In the medical device field, such devices are typically used for applying bioadhesives, polymers and other synthetic material used in wound closure. Because of the reactant nature of certain biocomponents used to form a bioadhesive, mixing of the components does not occur until immediately before the mixture is ready to be applied. Mixing of the components too soon before application may result in premature hardening of the mixture, thereby making application of the solution impossible. Thus, in these devices, the two or more components are maintained separately until just prior to application. While quick reaction of the components to form a sealant is quite good for its purpose, this characteristic poses challenges for delivery devices due to a high risk of clogging. For example, fibrin sealant delivery device dispensing tips can easily become non-functional due to clogging. To help address this challenge, typical delivery devices do not mix fibrin sealant components until they are just proximal to the dispensing end of the device. However, clogging remains a problem even with this approach due to residual components in the device after delivery.

Clogging is particularly a problem when there is intermittent use of a delivery device. Intermittent use may be required during a procedure for a variety of reasons, and the repeated starting and stopping of delivery often tends to clog the outlet of the applicator tip. As a result, most applicator assemblies are provided with a number of replacement tips for when clogging of the tip occurs. However, replacing clogged applicator tips interrupts the flow of a procedure, is time consuming and is an added expense. Previous methods and devices have incorporated features such as a flexible diaphragm or flexible flap tip, for example.

There is a need for an easy and reliable way to reduce clogging in a dispenser tip when not in use, even when rapidly-reacting materials are to be dispensed.

SUMMARY

The invention includes a device for mixing a first fluid and second fluid material prior to dispensing from a delivery tip. The device may include various components, including a dispensing device having a proximal end and a distal end and an outer surface, the dispensing device including a first lumen and a second lumen, each lumen having a proximal end, and a distal end, where the first lumen transports the first fluid and the second lumen transports the second fluid. The device may further include a cap and having an open proximal end, a distal end, and a circumferential sidewall connecting the proximal and distal ends, forming an open region between the proximal end and distal end, the proximal end of the cap being resiliently secured to the distal end of the dispensing device, and the distal end of the cap having an exit aperture extending through the distal end of the cap into the open space. The device defines a first volume within the open space of essentially zero formed by the mating of an inner surface of the distal end of the cap and the distal end of the dispensing device. The device further defines a second volume within the open space of greater than zero formed between the inner surface of the distal end of the cap and the distal end of the dispensing device when a force is applied to the cap.

The invention may include a device having a delivery tip, the delivery tip including a first fluid passageway and a second fluid passageway, each fluid passageway having an open distal end. The device may further include a mixing or swirl chamber including a headpiece, where the distal end of each fluid passageway is in fluid communication with the swirl chamber. The swirl chamber may include or may be a mixing area. The device further may include an expandable outer cover located around the swirl chamber, the expandable outer cover reduces the mixing area to zero volume in the absence of force acted thereon. The device includes an exit orifice in the expandable outer cover, which is open when force is acted on the expandable outer cover, through which fluid or fluids may be dispensed from the mixing area. The device may further include a pin which occupies the exit orifice in the absence of force acted on the expandable outer cover, thereby clearing the exit orifice of any fluid or fluids contained therein.

The invention further includes a method of using a delivery device. The method may include various steps, including devices as defined herein. The method includes the step of forcing a first fluid through first lumen and second fluid through second lumen. The method further includes the step of urging the first and second fluids through the open distal ends of first and second lumens. The method may also include the step of exerting pressure on the cap, thereby stretching the sidewalls of cap in a distal direction and moving the distal end of cap distally away from conical body, forming a mixing gap. The method includes mixing the first and second fluids within the mixing gap forming a resulting mixed product. Finally, the mixed product is ejected through the aperture.

BRIEF DESCRIPTION OF THE FIGURES

FIG. 2A shows an external view of the delivery device in a relaxed state. FIG. 2B shows a partial cut-away view of the delivery device of FIG. 2A.

FIG. 3A shows an external view of the delivery device in a stretched state.

FIG. 3B shows a partial cut-away view of the delivery device of FIG. 3A.

FIG. 5A shows a see-through view of an alternate embodiment of the delivery device of the present invention in a stretched state. FIG. 5B shows the embodiment of FIG. 5A in a relaxed state.

FIG. 9 shows a top perspective view of an alternate embodiment of a delivery device.

FIG. 10 shows a bottom perspective view of FIG. 9.

FIG. 11 shows a partial cut-away side view of a delivery device of FIG. 9.

FIG. 12 shows partial see-through side view of a delivery device of FIG. 9.

FIG. 13 shows a side view of the delivery tip of FIG. 9.

FIG. 14 shows a side view of the delivery tip of FIG. 9.

DETAILED DESCRIPTION

Figure 1:
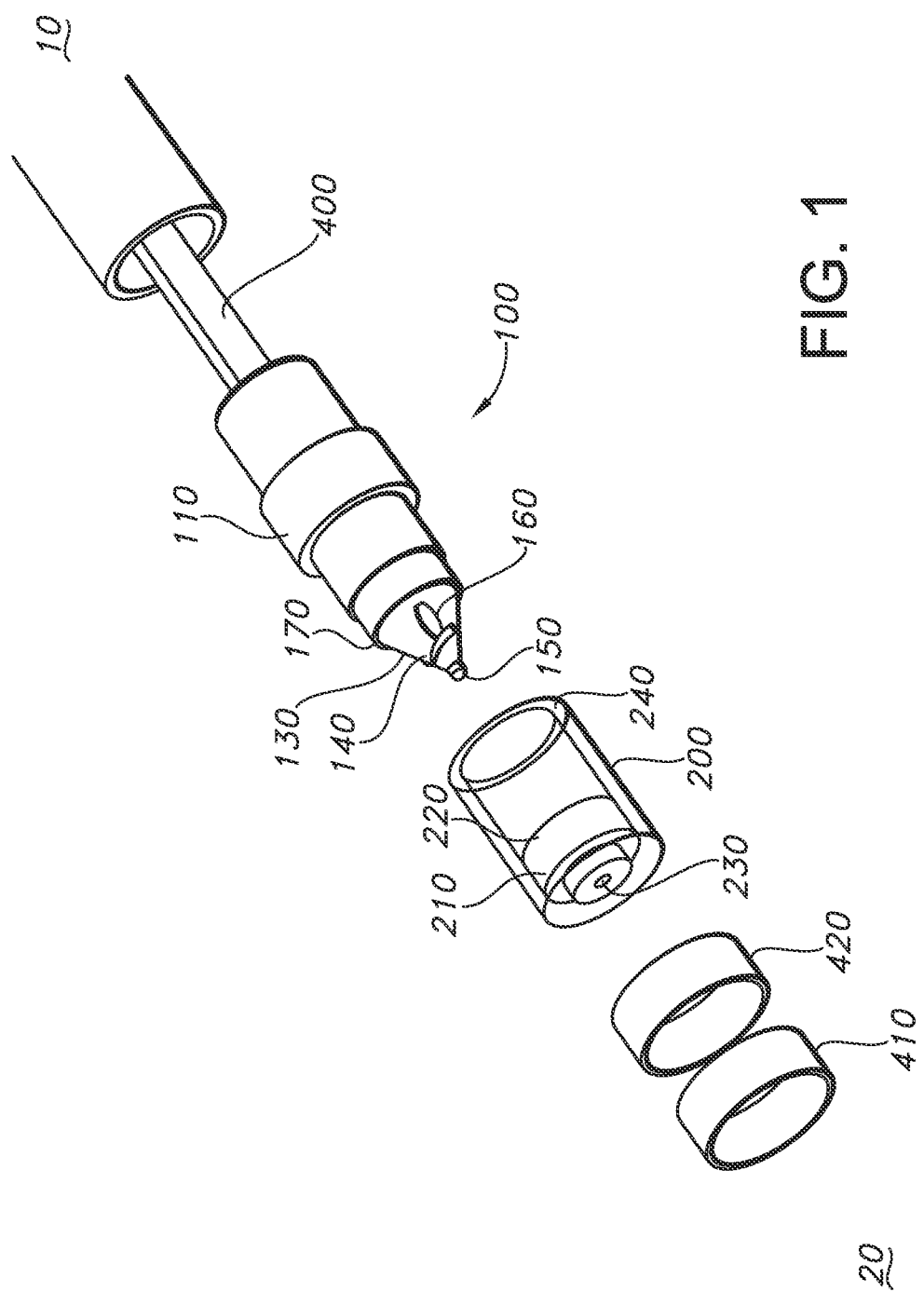
FIG. 1 depicts one embodiment of a delivery device of the present invention in exploded form.

With reference to the Figures, a delivery device for delivery of at least one, and more preferably two or more, fluid components is described. The two or more fluid components may be reactable components, and may be biological components. In a desired embodiment, the first fluid component is fibrinogen and the second fluid component is thrombin, which, when mixed together, react rapidly and form a fibrin sealant. Given the rapid rate at which the sealant is formed once the two components mix together, the mixing of components should occur immediately prior to dispensing at a target site. Further, if the mixing of two components occurs within the delivery device (as opposed to after ejection from the delivery device), a method for removal of the fluids, both reacted and unreacted, is helpful. The present invention provides a method and device for removal of fluids, reacted and unreacted, from the inside of a delivery device, more particularly for removal of fluids, reacted and unreacted, from the mixing chamber, when the device is not actively ejecting fluid.

In some aspects, the present invention includes a very small exit aperture, which provides controlled geometry as well as improved delivery. The present invention may also provide a swirling chamber for mixing fluids prior to ejection from the device. The use of a swirling chamber not only aids in mixing the fluids, but also allows the fluid and mixed materials to increase speed as each fluid is forced through and out a lumen. The swirl chamber allows the fluids to increase velocity entering a mixing chamber or mixing region, and may aid in providing sufficient speed to the materials upon exiting the delivery device to fragment into small droplets. The increased speed, in addition to the use of a small exit orifice, allows for dispensing of materials in a spray-wise manner without gas assist, if desired.

As will be explained in more detail below, the delivery devices of the present invention include a number of components, of which some or all may be used. Components that may be useful in the present invention include, for example, a delivery tip located at a distal end of a delivery device, such as a fluid flow conduit. The delivery tip may include a variety of configurations, including a conical head, spiral or helical walls, and angled walls for aiding in mixing and providing a spiral flow. Components also may include an axially expandable elastic cover or cap disposed about the delivery tip. The cover or cap may include a substantially rigid overmold component with an exit aperture located therein. These and other components are described in detail below.

FIG. 1 shows the various components of one embodiment of a delivery device of the present invention. The device includes a delivery tip 100, which has a generally cylindrical cross section, and may include an outwardly extending dispensing body 110. The delivery device has a proximal (or first) end, marked as reference numeral 10, and a distal (or second, or "dispensing") end, marked as reference numeral 20. The terms "proximal" and "proximal end" as well as "distal" and "distal end" will be used throughout this document, and refer generally to the directions explained above. Dispensing or delivery of the fluids occurs at or near distal end 20. The center of each component from its proximal end to distal end is referred to as its central axis.

The device may include, at its proximal end, a syringe system for dispensing fluids concurrently. A syringe system may generally include a barrel or barrels for housing fluids, a plunger to be inserted into each barrel, where depression of the plunger into the barrel forces fluid out of the distal end of the barrel, and a delivery conduit with delivery tip. The delivery device of the present invention may be used as a delivery tip of a general syringe system. The delivery tip may include a mixing or premixing chamber for mixing the fluids immediately prior to discharge, or the fluids may remain separate until discharged from the exit aperture. The delivery tip may include a swirl chamber for increasing the flow rate of the fluids.

Exemplary syringe-type devices include those described in U.S. Pat. Nos. 5,116,315, 5,605,255 and 6,063,055, which are each incorporated by reference herein in their entirety. The device taught in U.S. Pat. No. 5,116,315 discloses a system for delivery two fluids in a mixed composition, comprising a manifold and a discharge assembly. The discharge assembly mixes fluids in a mixing space and then atomizes the mixed fluids in a spray delivered from the assembly. Similarly, the device shown in U.S. Pat. No. 5,605,255 is an apparatus for spraying a liquid mixture having two syringes, a connecting piece, a premixing chamber, and a reduced volume section downstream from premixing chamber, and an exit aperture for spraying the mixture. The reduced volume section terminates in a homogenization region. U.S. Pat. No. 6,063,055 illustrates a device in which the mixing is performed in a mixing head. As mentioned above, these three U.S. patents are incorporated by reference herein in their entireties.

The present invention relates to the delivery tip of a device, which may be used in conjunction with a syringe type assembly as discussed above. A delivery lumen or manifold may extend from an aforementioned syringe body to the delivery tip, the delivery manifold including a plurality of internal lumens extending the axial length of the main delivery manifold. Each internal lumen is in fluid communication with a separate barrel, and is designed to transport a fluid material along the delivery lumen to the delivery tip. The proximal end of each lumen is in fluid communication with a barrel. The delivery tip of the present invention may be disposed at the distal end (20) of a delivery manifold. The delivery device need not necessarily include an elongated delivery lumen or manifold.

Referring back to FIG. 1, a delivery tip 100 includes outwardly extending dispensing body region 110, and may include a stepped region 120 (shown in FIGS. 2A, 3A) adjacent to the extended dispensing body region 110. Continuing in the distal direction (e.g., toward reference numeral 20), the delivery tip 100 includes a flange 170 connecting the stepped region 120 to a conical head 130, culminating in an axially extending tip 150 disposed substantially in the center of the head 130. The conical head 130 may include first and second fluid exit ports 160, which are each in fluid communication with a different fluid lumen. If desired, conical head 130 may include one or more helical or threaded regions 140, which act to force fluid into a spirally or helically moving fashion when ejected from the syringe and out each exit port 160. Alternatively, instead of a threaded or helical configuration, the conical head 130 may include outwardly extending angled regions, which also provide a degree of angled motion to fluids that are ejected from an exit port 160. Threaded/helical or angled regions 140 aid in mixing but also provide increased velocity to the fluids, aiding in proper dispensing from the device. Throughout the description, the head will be referred to as a conical head (130), but it is to be understood that the head may not be perfectly conical. In some aspects, the head 130 may take on a different, non-conical shape, such as bulbous, arced, or other configurations.

A cap or cover is provided to be securably placed onto the distal end of the delivery tip 100, the cap including a generally cylindrical body 200, the body 200 being made of a deformable, stretchable elastomeric material. The proximal end of the cylindrical body 200 has a generally open end, defined by a circumferentially surrounding end wall 240. The body 200 need not necessarily be cylindrical, but should be capable of providing an open interior at the proximal end of the delivery tip 100, with sidewalls running from proximal to distal ends, and includes a distal end. The body 200 may have a diameter of about 2-10 mm as measured from the outer surface of the sidewall, and in some aspects, including for laparoscopic methods, may have a diameter of about 5 mm as measured from outer surface of the sidewall.

Within the interior of the cylindrical body 200 and forming the distal end of the cylindrical body 200 is a substantially rigid overmold component 210, which may have a proximal flange 220. The overmold 210 has an opening extending from the interior of the cylindrical body 200 through an exit aperture or orifice or distal opening 230. Thus, distal opening 230 is in the overmold 210, and creates a fluid communication from the interior of the cylindrical body 200 to outside the cylindrical body 200. The cylindrical body 200 is sized and shaped to be placed over the delivery tip 100, such that the end wall 240 abuts against the extended region 110. The end wall 240 of the body 200 is secured to the delivery tip 100 by means of one or more retention rings, as described below. The interior of the overmold 210 is sized and shaped to receive the conical head 130, such that the extending tip 150 extends into and through the distal opening 230 when the two components are fully mated and in a relaxed state.

In some embodiments, the overmold 210 may have a generally saddle-type shape. The overmold 210 may be embedded within the cylindrical body 200, if desired. The overmold 210 can be secured to the cylindrical body 200 by snugly fitting overmold 210 inside the cylindrical body 200, by co-molding; or by use of an adhesive, as known to these skilled in the art. The overmold 210 need not span the entire distal end of the cylindrical body 200, but should be of sufficient size to provide proper alignment and sealing. The overmold 210 may have a generally flat distal surface, or it may have a conical or stepped configuration. The interior of the overmold 210 (that is, the side within the cylindrical body) should be shaped and sized to provide a suitable fit against the conical head 130. The interior may include one or more chemical or physical coatings, such as to promote anti-adhesion of sealant to the internal surfaces of components.

The distal opening 230 should be large enough to allow any of the fluids, including a resulting mixed composition, to be expelled from the delivery assembly. In some embodiments, the distal opening 230 may have a diameter of about 0.008 inches to about 0.015 inches, and more desirably about 0.010 inches. Larger openings may have a detrimental streaming effect, resulting in improper delivery, while smaller openings may unsuitably restrict the delivery of materials. Distal opening 230 should be sized properly to provide for atomization of fluids or resulting mixed materials, and allowing these materials to be sprayed as they exit the orifice under pressure. Distal opening 230 desirably has a generally circular cross section, but other cross sections may be used if desired.

It is particularly useful that the extending tip 150 and distal opening 230 have the same or similar cross section, so as to allow a snug and desirably fluid-tight fit when the tip 150 is inserted into the distal opening 230. Tip 150 may have a rounded distal end, or a sharp distal end, or it may be pointed or flat. Since the distal opening 230 is a part of the rigid overmold 210, it is preferred that the distal opening 230 be substantially constant in its diameter. That is, the act of force or pressure exerted in the device should not extend the diameter of the distal opening 230.

The delivery device includes a delivery tube 400, which is connected to the delivery tip 100, where the delivery tube 400 extends into the syringe-type applicator. The delivery tube 400 includes at least one, and preferably two internal fluid lumens (not shown) extending the axial length of the delivery tube 400 from proximal to distal end. Each internal fluid lumen is in fluid connection to the syringe at the proximal end, specifically with one fluid lumen being in communication with one fluid housing (such as a syringe barrel), and each internal fluid lumen is in fluid connection with one fluid exit port 160 at its distal end. Thus, fluid may travel from the syringe (more specifically, from a barrel of the syringe) through a fluid lumen, and out a fluid exit port 160.

Figure 4:
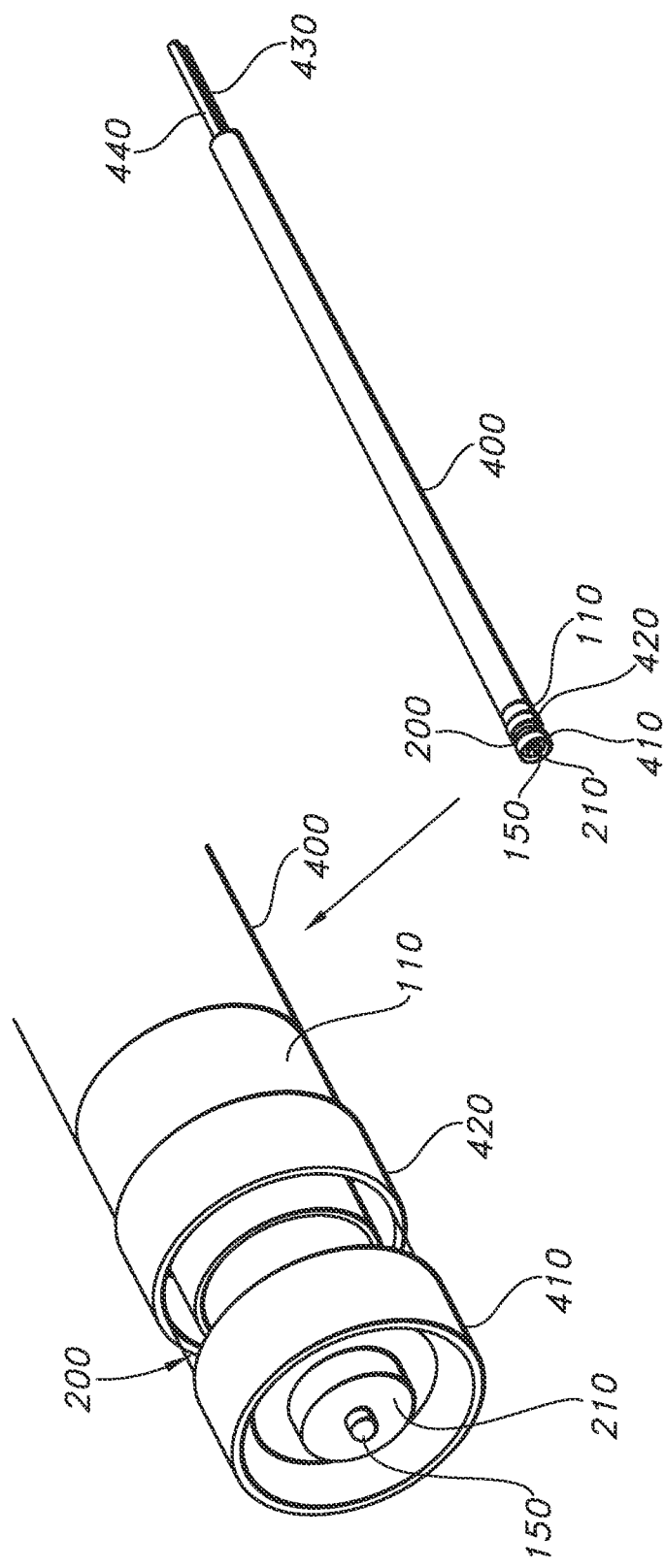
FIG. 4 shows the delivery device of FIG. 1 in assembled form.

If desired, the delivery device may include a first retention ring 410 and/or a second retention ring 420, as shown in FIG. 4, which are sized and shaped to fit snugly over the various components of the delivery device. Retention rings help to assure mechanical fixation of the cap 200 to tip 100, and of insert 210 to cap 200. Retention rings, if used, function as "crimp sleeves", applying inward radial pressure on the elastomeric part 200, capturing the elastomeric part between opposing rigid element. Rings may be made from rigid materials, such as stainless tubing, which provides high strength and has a relatively thin wall.

The cylindrical body 200 may be made of any desired materials, with the proviso that the material should be capable of being stretched in an axial direction (e.g., toward the distal end). Suitable materials include, for example, silicone, or other thermoset elastomers or thermoplastic elastomers. In one embodiment, the material forming the cylindrical body 200 includes a material having a 50-70 Shore A durometer reading. The body 200 may be transparent, translucent or opaque. The overmold 210 is desirably rigid, or at least substantially rigid, and desirably more rigid than the material forming the body 200. For example, the overmold 210 may be made from a hard plastic material with a hardness that is at least greater than the cylindrical body 200 by at least 10. The overmold 210 may be made from a hard plastic material, such that the geometry of the overmold 210 is not substantially distorted by fluid pressures generated during expression of fluid. Suitable materials for the overmold 210 include, for example, rigid thermoplastic resins such as polycarbonate, polyamides, ABS, and the like.

FIGS. 2A-2B show one embodiment of the delivery assembly in a relaxed state. While in the relaxed state, no pressure is being actively exerted on the delivery assembly, and therefore the distal opening 230 is closed. More preferably, the distal opening 230 is closed or occluded by inserting the tip 150 through the distal opening 230, as can be seen in FIG. 2A. In the relaxed state, the cylindrical body 200 is secured over the outer circumference of at least a portion of the delivery tip 100, with the end wall 240 mating with the wall of the outwardly extending region 110. Thus, the conical head 130, with fluid lumen openings 160 are housed within the periphery of the cylindrical body 200. Also, in the relaxed state, the proximal end of the overmold 210 may be pressed against the flange 170. The overmold 210 is also pressed against the conical head 130, such that there is no space or gap between the conical head 130 and the overmold 210. The tip 100 has no gaps, openings or free regions between the components of the delivery tip 100 and the cylindrical body 200 or overmold 210. Put another way, when the body 200 is in a relaxed state, there is little to no volume of free space ("mixing volume") within the cylindrical body 200.

FIGS. 3A-3B show the delivery assembly in a stretched or dispensing state. As can be seen, cylindrical cap 200 is stretched axially. The stretching of cylindrical cap 200 may be achieved through the force exerted when fluid or fluids are pressed from the syringe into the delivery tip assembly under pressure. Fluids are forced into the delivery assembly via exit ports 160, where the fluid/fluids exert pressure from the interior of the cylindrical body 200. As can be seen, the sidewalls of the cylindrical body 200 are stretched in the distal direction (e.g., in the direction of the arrow A). Since it is secured to the cylindrical body 200, stretching the walls of the cylindrical body 200 move the overmold 210 in the same direction, e.g., the distal direction. Movement in the distal direction causes the overmold 210 to move in the distal direction, thereby creating separation between it and the conical body 130, and forming gap (or open volumetric region) 300 therebetween. When the body 200 is in a stretched or dispensing state, there is an increase in the volume of free space in the body 200, thereby creating a suitable mixing volume within the dispensing assembly. The axial length of stretch due to application of force may be from about 0.01 inches to about 0.06 inches.

The presence of the gap 300 allows fluids to flow through exit ports 160, and into the gap 300. Since the fluids are being exerted under force and pressure, they travel out the exit ports 160 and therefore are able to react with each other, forming a resulting mixed product. Further, if the fluids are caused to move in a spiral fashion by helical or angled regions 140, the fluid velocity while in the mixing gap 300 is increased. Movement in a spiral or helical fashion, while under pressure, helps the mixing and dispensing of first and second fluids (and any other fluids exerted simultaneously). This results in efficient mixing and the ability to properly dispense a reacted material directly onto the target site out of the distal opening 230. The opening or gap 300 may have any desired volumetric size, with the proviso that the opening should be large enough to allow for mixing of fluid components therein. In some embodiments, the gap 300 may have a size of at least about 0.4 mm$^3$.

The mixing volume (i.e., the size of gap 300) is created as a result of the pressure exerted by forcing fluid components into the gap 300 space, causing stretching of the cylindrical body 200 while the cylindrical body 200 is secured to the dispensing tip 100 (such as via retention ring 420). The gap 300 will remain open for so long as sufficient pressure is applied against the cylindrical body 200. In the absence of sufficient pressure, such as by ceasing pressure on the fluids into the delivery assembly, the cylindrical body 200 may contract to its resting state, reverting the assembly to the "resting" position described in FIGS. 2A-2B. Reverting to the resting position closes the device and clears out residual fluid and resulting mixed materials, expelling residual fluid and resulting mixed materials through distal opening 230.

FIG. 4 shows a delivery device and a close-up of the delivery head of the delivery device. In the device of FIG. 4, an elongated tube 400 is used, with the delivery tip 100 as described above at its distal end (20). In the closed state, e.g., when no force is acted on the cylindrical body 200, the axially extending tip 150 extends through the distal opening 230, not only blocking fluids from passing through the distal opening 230 after the distal opening 230 plugged by extending tip 150, but as extending tip 150 extends through the opening 230, it forces out any residual fluids or materials that may have been contained within the distal opening 230.

During use, such as during force applied to the fluids in the distal direction, the fluid components are mixed in the mixing space (gap 300), and the resulting mixture is forced under pressure out the distal opening 230, where the resulting mixture is applied to a desired target site. Since the mixture is to be dispensed directly onto or in the area of a target site, before pressure is exerted on the fluids, it is desirable to align the distal opening 230 with a target site, such as a wound site or other suitable delivery site. It is particularly useful to deliver the resulting mixed material directly to the intended site when the fluids are biological fluids, such as a first fluid of thrombin solution and second fluid of fibrinogen solution, where the resulting mixed material is fibrin. The reaction of these two biological components occurs quite rapidly, and direct application of the recently-mixed product is important to provide proper delivery and sealing. The present invention may be capable of dispensing a mixed composition without the need for gas to be used to expel and further mix the fluid or fluids, and may be capable of dispensing the mixed composition in a spray wise delivery without the need for gas assistance. It is to be understood that other two-part sealants, adhesives, or hemostatic agents can be used, both biologics based, and non-biologics based, and such two-part sealing and/or hemostatic compositions are well known to these skilled in the art.

When the delivery of reacted material is to be stopped, whether because the user has dispensed enough material, or because the user wishes to move to a different target site, or because the fluid(s) to be dispensed have to be replaced or refilled, it is quite helpful to have a delivery tip that reduces clogging. As noted above, the reaction of certain fluids, such as fibrinogen and thrombin, occurs very quickly and results in an adhesive sealant. As such, those of ordinary skill in the art will understand that residual fluid left in a dispensing tip, particularly in the mixing area or mixing chamber of the dispensing tip, will have a tendency to form the sealant while still within the tip. Unless fluid materials, including the starting materials and reacted materials, are removed from the inside of the delivery tip, clogging will be expected. Clogging renders the delivery tip to be of limited use, and requires changing the tip, or at the very least will require subsequent cleaning and removal of fluids or materials, which is a time-consuming and difficult step to achieve.

With the present device, including delivery tip 100 and cylindrical body 200, quick and efficient removal of fluids can be achieved with no additional effort by the user. Once the user ceases exerting pressure, such as through pressing on a syringe as described above, the cylindrical body 200 begins to revert back to a relaxed state. As the cylindrical body 200 reverts to a relaxed state, the walls of the body 200 compress axially, pulling the overmold 210 back in the proximal direction, where it reduces the volumetric size of the gap 300, and the interior of the overmold 210 contacts the conical head 130. As the size of gap 300 is reduced, fluids, including mixed components, are forced out of the distal opening 230. These fluids and mixed components are forced out of the distal opening 230 until the volumetric size of the gap 300 is at or near zero.

At this point, all or a significant amount of fluid or fluids, including mixed components, have been removed from the interior of the cylindrical body 200, and desirably the overmold 210 is substantially in contact with the conical head 130. To ensure that there are little or no remaining fluids blocking the distal opening 230, the conical head 130 is equipped with the axially extending tip 150, which is urged through and out the distal opening 230 as the cylindrical body 200 is compressed axially. Most desirably, the outer circumference of the axially extending tip 150 is approximately equal to the inner circumference of distal opening 230, such that it fits snugly through the opening 230. It may be desired that the axially extending tip 150 have a larger diameter than the distal opening 230, but that the axially extending tip 150 be capable of being compressed to snugly fit within the distal opening 230. It is particularly desirable that the outer circumference of the axially extending tip 150 substantially or fully contact the inner circumference of distal opening 230, thereby pushing or urging any remaining sealant out of the distal opening 230 and blocking exit or entry through the distal opening 230. The present invention provides automatic purging of residual fluids, including biological fluids and resulting mixed compositions, upon the cessation of fluid expression.

The present invention provides a delivery assembly, which in a resting state (i.e., without the act of force thereon), provides a zero-volume, or near-zero-volume region between the conical head 130 and the overmold 210. This configuration therefore avoids the creation of a resulting mixed product, such as fibrin, within the created volumetric space after pressure is removed from the lumens carrying the fluid materials.

This allows a user to clear residual unreacted, reacted, or cured fluids within the dispensing assembly with subsequent biologic sealant expression. If any small quantities of reacted material (e.g., fibrin) happen to form within the volumetric space 300 and remain in this space after contraction of the cylindrical body 200, such small quantities will quickly be expelled out the distal opening 230 upon subsequent application of pressure on the lumens carrying the biologic materials.

The cylindrical body 200 is desirably capable of being stretched in the axial direction (proximally and distally) a plurality of times, such that the delivery assembly can be used repeatedly. Most preferably, the cylindrical body 200 may be stretched at least 25 times, at least 50 times, at least 100 times or at least 1000 times without loss of elasticity or without breaking. Further, the retention rings 410, 420 should be sufficiently durable to allow for repeated use, including maintaining position of the cylindrical body 200, for at least the same number of times that the cylindrical body 200 is stretched and contracted.

FIGS. 5A and 5B show an alternate configuration of a delivery tip in a dispensing state (FIG. 5A) and in a closed state (FIG. 5B). Similar to the device as described above, the dispensing device includes a delivery conduit or lumen 500, which contains within its periphery a first fluid lumen 510 and second fluid lumen 520. The tip includes an outwardly extending ring 530, which abuts with a cover 540. The cover includes a distal opening 550, through which fluids or reacted materials can be expelled from the delivery device. As can be seen in FIG. 5A, first fluid 515 and second fluid 525 travel through their respective lumens (first fluid lumen 510 and second fluid lumen 520), into the open space encompassed by the cover 540, and are expressed through the distal opening 550. Although not seen in the Figures, the proximal ends of each lumen 510, 520 are in communication with a barrel or other fluid-containing device. When in the closed position, as seen in FIG. 5B, an extended tip 560 protrudes through the distal opening 550, thereby removing residual materials within the distal opening 550 and blocking flow of fluid through the distal opening 550.

Figure 6:
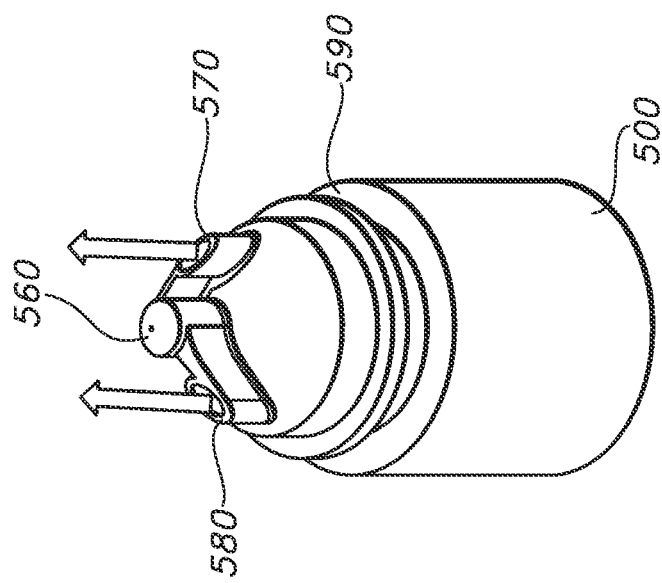
FIG. 6 shows a perspective view of a sealant cap of the present invention.

FIG. 6 shows another possible configuration for a delivery tip, including the same general components as described above. As can be seen, the delivery tip includes an outwardly extending ring 530, a cover 540, and an opening 550. The tip of FIG. 6 also includes a separate overmold 545, which is located at the distal end of the cover 540. The opening 550 is located in and through the overmold 545, and provides fluid communication from the inside of the cover 540 to outside the delivery device. If used, an overmold 545 is more rigid than the cover 540, thereby allowing the cover 540 to be expanded under pressure but maintaining the structure and rigidity of the overmold 545.

Figure 7:
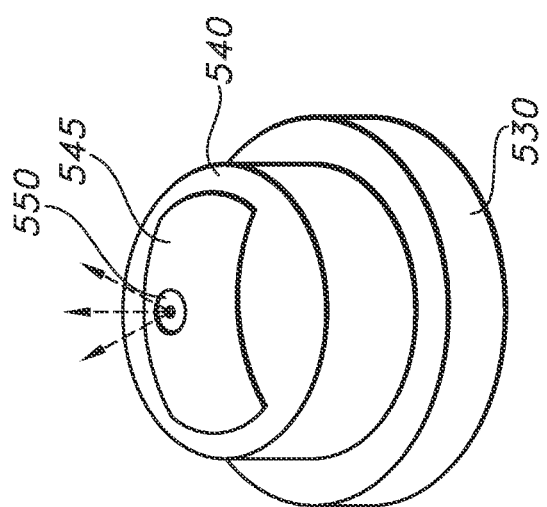
FIG. 7 shows a side view of a delivery tip of the present invention.
Figure 8:
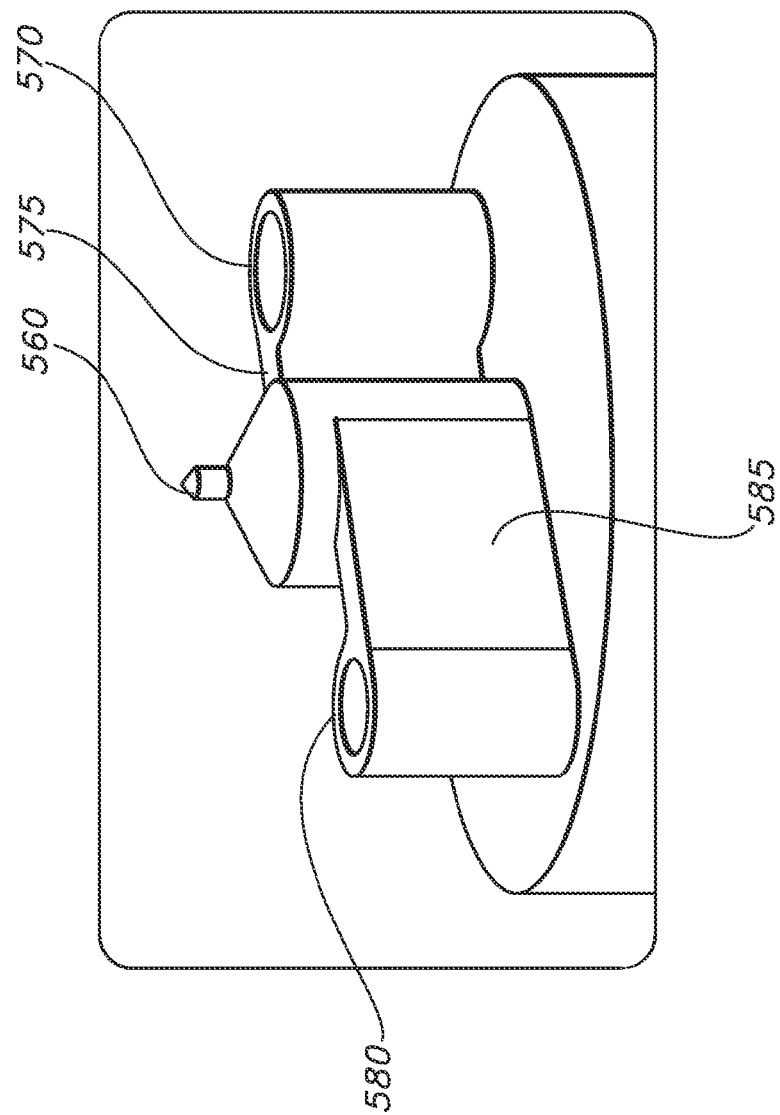
FIG. 8 shows a close up view of the delivery tip of FIG. 7.

FIG. 7 shows a dispensing device useful in the present invention. The dispensing device may be used with any of the delivery tips or covers described above. The dispensing device of FIG. 7 includes lumen 500, which includes at its distal end a first fluid opening 570 and a second fluid opening 580. The first fluid opening 570 is at the distal end of the first fluid lumen 510, while the second fluid opening 580 is at the distal end of the second fluid lumen 520. As can be seen, first fluid 515 exits the first fluid opening 570 and second fluid 525 exits the second fluid opening 580. Dispensing device in FIG. 7 includes an extended tip 560. As can be seen in FIG. 8, which is a close-up view of the distal end of mixing device of FIG. 7, the first fluid opening 570 may be in association with a first angled wall 575, and second fluid opening 580 may be in association with a second angled wall 585. The use of angled walls (575, 585) may be useful in mixing the fluids as they are forced out of their respective lumen openings and into the mixing chamber. The fluids are moving under force, and with angled walls, turbulence or rotational mixing may be achieved. Further, the use of angled walls (575, 585) aids in increasing the velocity of the fluids as they are forced through the dispensing device, and aids in proper delivery through the opening 550.

FIGS. 9-14 show another depiction of a delivery tip, which includes the general features and components described above. The delivery tip includes shaft 500, having first fluid lumen 510 and second fluid lumen 520 extending therethrough. At the distal end of the shaft 500 is an outwardly extending ring 530, with expandable cover 540 secured thereto. At the distal end of cover 540 is an overmold 545, with an exit opening 550 extending therethrough, as explained above. As can be seen in FIGS. 12-14, the device includes a flange 590, against which the cover 540 may abut to form the proximal end of the mixing open space or mixing chamber. As seen in FIG. 14, the distal end of the mixing device includes an extended tip 560, first fluid opening 570, second fluid opening 580, first angled wall 575 and second angled wall 585. Angled walls 575, 585 may be replaced with other mixing aids, including, for example, helical threads or raised portions, or ridges to aid in agitation and mixing.

The interior of the distal end of the cover 540, including the overmold 545, desirably abuts the distal end of the mixing device, including first and second fluid openings 570, 580, when the device is in the "closed" position. Therefore, the internal region of the overmold 545 should be shaped and sized so as to mate with the distal end of mixing device to allow closure of the gap therebetween. When force is acted on the cover 540, it stretches axially in the distal direction, creating an opening or mixing chamber, into which the fluids are ejected and can mix. The pressure caused by force enacted on the fluids causes mixing and ejection of the mixed material through opening 550. When pressure is removed, the cover 540 ceases stretching, and returns to its desired, relaxed state, in which the overmold 545 is pulled back into the proximal direction. When in the proximal direction, the overmold 545 abuts the mixing device, forcing residual fluid or materials out of opening and closing fluid openings 570, 580.

The present invention provides a method of dispensing a multi-fluid material, where the fluids react with each other to form a resulting reacted material or reacted composition. First and second fluids are housed in separate compartments, such as in barrels of a syringe. When pressure is exerted on the barrels, such as in a representative syringe-type assembly, each fluid travels through its own fluid lumen, into a delivery tip 100. At the end of delivery tip 100 is a conical head 130, having a first lumen opening 160 and second lumen opening 170 associated therewith. Conical head 130 may have a mixing and dispensing aid, such as helical ribs or angled walls 140, and may have axially extending tip 150. Surrounding the outside of the delivery tip 100 is elastic cover 200, including overmold 210 and opening 230 as explained above.

In use, as the fluids are forced through lumens into the delivery tip 100, pressure is generated due to the force enacted on the fluids, thereby causing distal stretching of the sidewalls of the cylindrical body 200. As the sidewalls stretch distally, the distal end of the cylindrical body 200, including overmold 210, is moved in the distal direction, thereby opening the gap 300 between conical head 130 and overmold 210. First and second fluids are then able to be ejected from first and second lumen openings 160, 170, respectively, and enter the gap 300. Due to the pressure and force enacted on the fluids, they move within the gap 300 and are allowed to mix with each other, forming a resulting mixed material or composition. If the device includes a mixing and dispensing aid (such as helical or angled wall 140), the fluids move at an increased velocity and/or with added directionality of movement resulting in improved intermixing during the mixing process and may result in spray-wise delivery.

As the overmold 210 has been moved distally, the distal opening 230 is opened and is in fluid communication with the gap 300. First and second fluids, and resulting mixed material, are ejected through the distal end of the device through opening 230. It is desired that the first and second fluids are fully mixed with each other prior to being ejected from opening 230, but it is understood that some residual first and/or second fluid may be released from the opening 230. Given the near-immediate reaction between certain chemistries, such and thrombin and fibrinogen, even if some residual first or second fluid is ejected through opening 230, it is likely to react soon after being released from the device. The ejected materials are applied directly to the intended site, such as site of a wound or surgical site. Depending upon the level of force generated on the fluids, and additionally whether a dispensing aid such as angled/helical walls 140 is used, the materials may be atomized upon ejection from the opening 230.

As the user releases pressure, such as by ceasing depressing a syringe or a dual-barrel syringe, the first and second fluids stop being forced out of the delivery tip 100, and therefore, the pressure exerted on cylindrical body 200 is reduced or stopped altogether. With the lack of pressure and force, the sidewalls of the cylindrical body 200 are allowed to contract to their initial, relaxed state, thereby pulling the overmold 210 in the proximal direction. Pulling the overmold 210 proximally towards the conical head 130 reduces the gap 300, and forces residual fluid or reacted materials out of the distal opening 230. Desirably, the internal side of the overmold 210 intimately mates with the conical head 130, creating a near-zero volume size therebetween, essentially squeezing any residual materials out through the opening 230. Further, in some aspects, the conical head 130 includes an axially extending tip 150, which is snugly fit through the distal opening 230, removing additional residual material (fluids or reacted materials) from the device, and additionally blocking the distal opening 230 when not in use. When the device is to be used again, due to the removal of fluids or materials, there is little or no fluids or other materials remaining in the gap 300, and there is little to no materials blocking or clogging the distal opening 230.

The present invention promotes thorough mixing of fluids before expression from the delivery tip, which results in improved mechanical properties and a faster set time, with less run-off. The use of the mating between overmold and conical head, in addition to the axially extending tip (if used) provides automatic purging of residual materials or fluids, and gives the ability to clear residual mixed components, including cured materials such as sealants.

Figure 15:
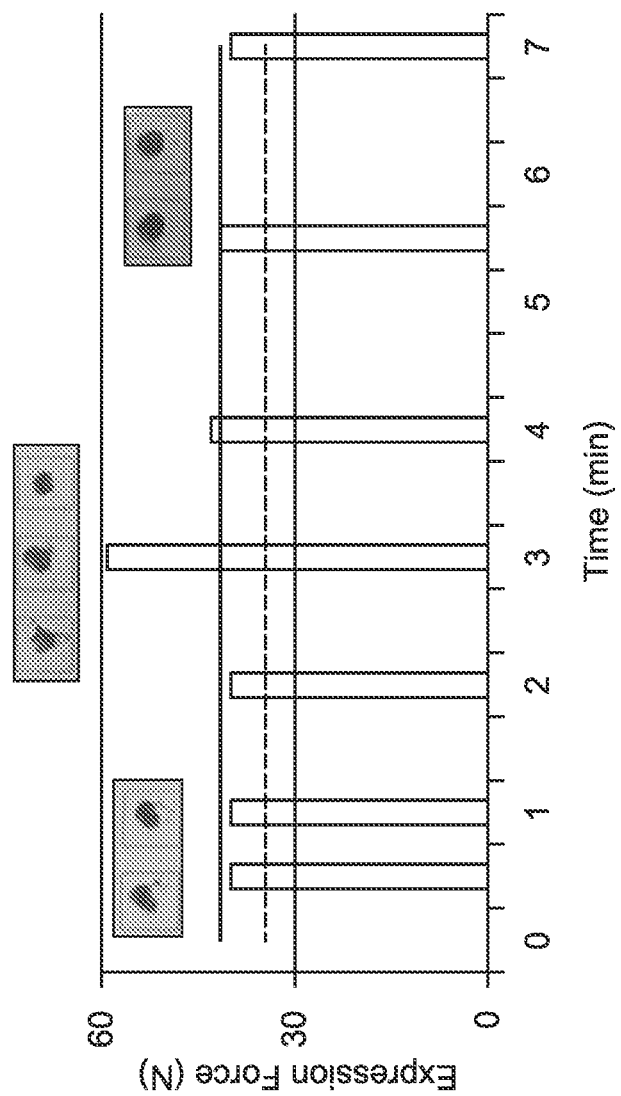
FIG. 15 shows a graph of the results of an Example using the delivery device of FIG. 9.

As depicted in FIG. 15, a prototype delivery device, similar to that of FIG. 9, was used to mix and express biologic material after various time pauses. Solutions of thrombin and fibrinogen were mixed using the prototype delivery device and expressed in a burst mode with various time delays or pauses between expression bursts. Specifically, the fibrin sealant formed by mixing of the thrombin and fibrinogen solutions was expressed with interruptions/pauses, including second pauses, sixty second pauses, and ninety second pauses, with the expression force in Newtons plotted against expression time in minutes, each bar corresponding to a burst of expression, with the gap between bars showing expressions interruptions/pauses. As can be seen in the FIG. 15, there was not a significant increase in expression force after various interruption or pause time periods over a total experiment time of seven minutes, with total number of seven expression bursts separated by 30 s interruptions/pauses (first two bars on the chart), 60 s interruptions/pauses (interval between second & third, third & fourth, fourth & fifth bar on the chart), 90 s interruptions/pauses (interval between fifth & sixth, sixth and seventh bar on the chart) interruptions/pauses. The data indicates that there was little to no clogging or blockage of the delivery device between uses.

EXAMPLES

As an example of a device useful in achieving mixing of two materials and dispensing of the resulting mixed material, the device includes a delivery tip including: (i) a dispensing device having a proximal end and a distal end and an outer surface, the dispensing device including a first lumen and a second lumen, each lumen having a proximal end, and a distal end, where the first lumen transports the first fluid and the second lumen transports the second fluid; (ii) a cap having an open proximal end, a distal end, and a circumferential sidewall connecting the proximal and distal ends, forming an open space between the proximal end and distal end, the proximal end of the cap being resiliently secured to the distal end of the dispensing device, and the distal end of the cap having an exit aperture extending through the distal end of the cap into the open space, (iii) a first volume within the open space of essentially zero formed by the mating of an inner surface of the distal end of the cap and the distal end of the dispensing device; and (iv) a second volume within the open space of greater than zero formed between the inner surface of the distal end of the cap and the distal end of the dispensing device when a force is applied to the cap.

In the device of the example described above, the second volume may be created due to the displacement of the cap with respect to the distal end of the dispensing device.

In the device of either of the examples described above, the circumferential sidewall may be axially stretchable.

In the device of any of the examples described above, the cap may have an overmold.

In the device of any of the examples described above, the exit aperture may be in the overmold.

In the device of any of the examples described above, the side walls may extend around the outside of the dispensing device.

In the device of any of the examples described above, the cap may be held in place by at least one retaining ring.

In the device of any of the examples described above, the second volume may be about 0.4 mm$^3$.

In the device of any of the examples described above, the distal end of the dispensing device may include a conical body.

In the device of any of the examples described above, the interior surface of the overmold may be sized and shaped to mate with the conical body.

In the device of any of the examples described above, the conical body may include an axial and distally extending tip.

In the device of any of the examples described above, the distally extending tip may fit snugly within the exit aperture.

In the device of any of the examples described above, force may be applied by pressurizing fluids through lumens.

In the device of any of the examples described above, the dispensing device may include cyclonic mixing.

In the device of any of the examples described above, the first fluid may include fibrinogen and the second fluid includes thrombin.

In another example, there is a method of using the device of any of the examples described above.

In the method described in the example above, the method may include the steps of: (i) forcing a first fluid through first lumen and second fluid through second lumen; (ii) urging the first and second fluids through the open distal ends of first and second lumens; (iii) exerting pressure on the cap, thereby stretching the sidewalls of cap in a distal direction and moving the distal end of cap distally away from conical body, forming a mixing gap; (iv) mixing the first and second fluids within the mixing gap forming a resulting mixed product; and (v) ejecting the mixed product through the aperture.

In the method of any of the examples described above, the pressure on the cap may be caused by the fluids being forced out of the open distal ends of first and second lumens.

In the method of any of the examples described above, the mixing gap may be the open space.

In the method of any of the examples described above, the first fluid may include fibrinogen and the second fluid includes thrombin.

In the method of any of the examples described above, the resulting mixed product may be fibrin.

In the method of any of the examples described above, the method may further include the step of aligning the aperture with a target site prior to ejecting the mixed product.

In the method of any of the examples described above, the target site may be the site of a wound or a surgical site.

In another example, there is a dispensing apparatus including a delivery tip, the delivery tip including: (i) a first fluid passageway and a second fluid passageway, each fluid passageway having an open distal end; (ii) a swirl chamber including a headpiece, where the distal end of each fluid passageway is in fluid communication with the swirl chamber; (iii) a mixing area within the swirl chamber; (iv) an expandable outer cover located around the swirl chamber, the expandable outer cover reduces the mixing area to zero volume in the absence of force acted thereon; (v) an exit orifice in the expandable outer cover, which is open when force is acted on the expandable outer cover, through which fluid or fluids may be dispensed from the mixing area; and (vi) optionally, a pin which occupies the exit orifice in the absence of force acted on the expandable outer cover, thereby clearing the exit orifice of any fluid or fluids contained therein.

In the apparatus of the example above, when the mixing area is zero volume, the cover may shut off flow from each passageway.

In the apparatus of any of the examples above, the pin may be on the headpiece.

In the apparatus of any of the examples above, the expandable outer cover may have a distal end, an open proximal end, and circumferential sidewalls.

In the apparatus of any of the examples above, the exit orifice may be at the distal end of the cover.

In the apparatus of any of the examples above, the cover may include a rigid overmold at the distal end.

In the apparatus of any of the examples above, the interior surface of the overmold may mate with the headpiece.

In the apparatus of any of the examples above, retention rings may connect the cover to the headpiece.

In the apparatus of any of the examples above, the device may further include a swirl chamber formed by the circumferential sidewalls, the distal end of the cover and the headpiece.

In the apparatus of any of the examples above, the swirl chamber may include helical or angled walls to aid swirling of fluids within the swirl chamber.

What is claimed is:

1. A device for mixing a first fluid and a second fluid prior to dispensing from a delivery tip comprising:
   (i) a dispensing device having a proximal end and a distal end and an outer surface therebetween, the dispensing device comprising a first lumen and a second lumen, each lumen having a proximal end and a distal end, wherein the first lumen transports said first fluid and said second lumen transports said second fluid, the dispensing device further comprising a delivery tip at the distal end comprising a conical head;
   (ii) a cap having an open proximal end, a distal end, and a circumferential sidewall connecting the proximal and distal ends, the cap forming an open space between said proximal end and distal end, the cap being resiliently secured to the distal end of the delivery tip, and the cap comprising an overmold having an exit aperture extending through the distal end of the cap into the open space, the overmold comprising an interior, the interior being configured to receive the conical head of the delivery tip when the delivery tip and cap are mated, (iii) a first volume within the open space of essentially zero formed by the mating of an inner surface of the distal end of the cap and the delivery tip at the distal end of the dispensing device, the first volume being created by no gap between the overmold and the conical head when the delivery tip and cap are mated; and (iv) a second volume within the open space of greater than zero formed between the inner surface of the distal end of the cap and the delivery tip at the distal end of the dispensing device, the second volume being created by a mixing gap between the overmold of the cap and the conical head of the delivery tip when a pressure is applied to the cap, wherein said pressure on the cap is caused by the fluids being forced out of the distal ends of the first and second lumens.

2. The device of claim 1, wherein the second volume is created due to the displacement of the cap with respect to the distal end of the dispensing device.

3. The device of claim 1, wherein the circumferential sidewall is axially stretchable.

4. The device of claim 1, wherein the exit aperture is in the overmold.

5. The device of claim 1, wherein the side walls extend around the outside of the dispensing device.

6. The device of claim 1, wherein the cap is held in place by at least one retaining ring.

7. The device of claim 1, wherein the conical head includes an axial and distally extending tip, wherein the distally extending tip is configured to fit snugly within the exit aperture.

8. A method of dispensing a mixed product through the device of claim 1, said method comprising:

(i) forcing the first fluid through the first lumen and the second fluid through the second lumen;

(ii) urging said first fluid and said second fluid from the first lumen and the second lumen;

(iii) exerting pressure on the cap, thereby stretching the circumferential sidewall of the cap in a distal direction and moving the distal end of cap distally away from conical body, forming a mixing gap;

(iv) mixing said first fluid and said second fluid within said mixing gap forming a resulting mixed product; and (v) ejecting said mixed product through said exit aperture.

9. The method of claim 8, wherein said mixing gap is the open space.

10. The method of claim 8, further comprising aligning the exit aperture with a target site prior to ejecting said mixed product.

* * * * *